US00PP29573P3

(12) United States Plant Patent
Wood

(10) Patent No.: US PP29,573 P3
(45) Date of Patent: Aug. 7, 2018

(54) ***VIBURNUM* PLANT NAMED 'SMNVDMDO'**

(50) Latin Name: *Viburnum dilatatum*
Varietal Denomination: SMNVDMDO

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 41 days.

(21) Appl. No.: 15/530,099

(22) Filed: Dec. 2, 2016

(65) Prior Publication Data

US 2018/0160596 P1 Jun. 7, 2018

(51) Int. Cl.
*A01H 5/02* (2018.01)
*A01H 5/12* (2018.01)

(52) U.S. Cl.
USPC ..... Plt./226
CPC ..... *A01H 5/02* (2013.01); *A01H 5/12* (2013.01)

(58) Field of Classification Search
USPC ..... Plt./226
See application file for complete search history.

*Primary Examiner* — Anne Marie Grunberg
(74) *Attorney, Agent, or Firm* — Cassandra Bright

(57) ABSTRACT

A new and distinct *Viburnum* plant named 'SMNVDMDO' is disclosed, characterized by abundant distinctively orange fruits. Plants have strong, vigorous growth and flower abundantly in containers, producing full plants with good flower coverage. The new variety is a *Viburnum* normally produced as an outdoor garden or container plant.

3 Drawing Sheets

Latin name of the genus and species: *Viburnum dilatatum.*
Variety denomination: 'SMNVDMDO'.

BACKGROUND OF THE INVENTION

The present invention comprises a new and distinct variety of *Viburnum*, hereinafter referred to by the cultivar name 'SMNVDMDO'. This new *Viburnum* was developed through a breeding program in Grand Haven, Mich. The objective of the breeding program was to develop new *Viburnum* varieties orange fruits. 'SMNVDMDO' was selected from a population of seedlings grown from seed resulting from the crossing of the seed parent *Viburnum dilatatum* 'Michael Dodge', unpatented, with *Viburnum dilatatum* 'Henneke', U.S. Plant Pat. No. 12,870. The crossing resulting in the new variety was conducted during 2005. Selection of the new variety was made during 2010.

The first asexual propagation of 'SMNVDMDO' was carried out during 2010 by softwood cuttings at a commercial nursery in Grand Haven, Mich. 'SMNVDMDO' has been found to retain its distinctive characteristics through successive asexual propagations. Multiple generations have been propagated, with the new variety characteristics reproduced true to type.

SUMMARY OF THE INVENTION

The following are the most outstanding and distinguishing characteristics of this new cultivar when grown under standard horticultural practices at Grand Haven, Mich.:

1. Orange fruit in the Fall.
2. Full, dense plant.
3. Strong, vigorous growth.
4. Floriferous plants in container production.

COMPARISON WITH THE PARENT VARIETIES

'SMNVDMDO' is distinguished from its female parent *Viburnum* 'Michael Dodge' in the following:

1. The new variety produces orange fruit, the seed parent produces yellow fruit.
2. Mature height of the new variety is 6 to 9 feet, mature height of the seed parent is 5 to 6 feet.
3. The new variety produces larger leaves than 'Michael Dodge'.

'SMNVDMDO' is distinguished from its male parent *Viburnum* 'Henneke' in the following:

1. The new variety produces orange fruit, the pollen parent produces red fruit.
2. Mature height of the new variety is 6 to 9 feet, mature height of the seed parent is 6 to 8 feet.

COMMERCIAL COMPARISON

'SMNVDMDO' is similar to the commercial variety *Viburnum* 'Erie', unpatented, in most horticultural characteristics. 'SMNVDMDO' however differs in the following:

1. Plants of the new variety produce orange fruit, plants of 'Erie' produce red fruit.

DESCRIPTION OF THE PHOTOGRAPHS

This new *Viburnum* is illustrated by the accompanying photographs which show the plant's form, foliage and inflorescences. The colors shown are as true as can be reasonably obtained by conventional photographic procedures. Plants were grown in Grand Haven, Mich.

Figure 1:
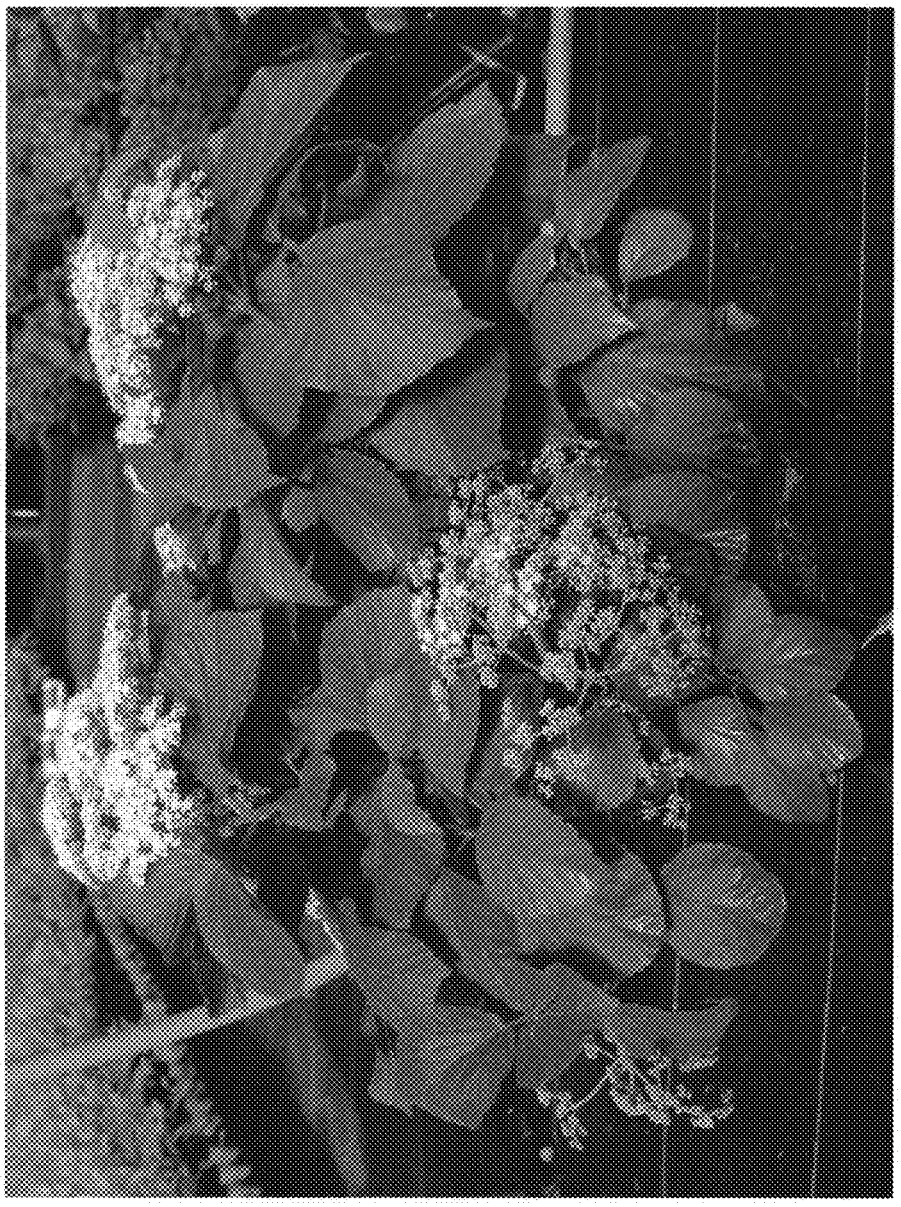

FIG. 1. Shows a flowering plant of 'SMNVDMDO' in a 3 gallon container at approximately 2 years old during Summer. Plants were grown in a polyhouse.

Figure 2:
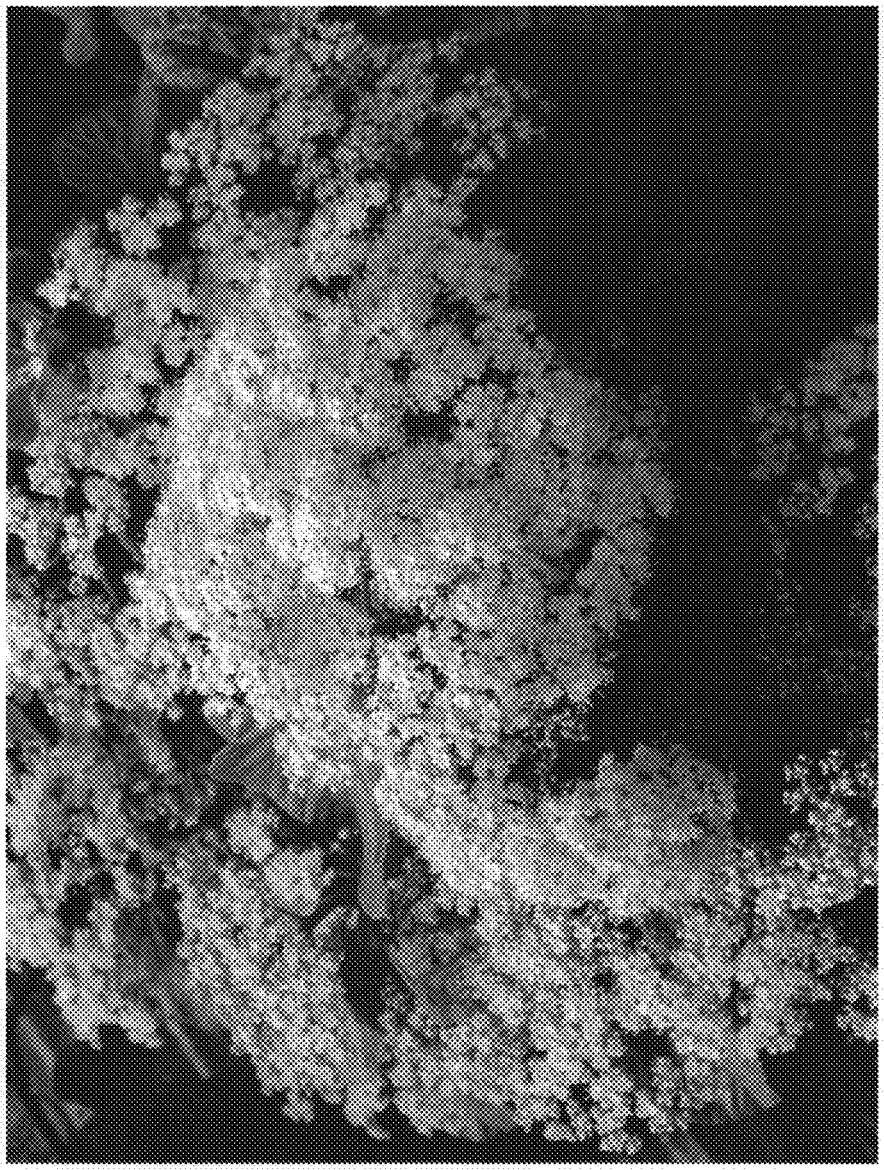

FIG. 2. Shows a close-up view of flowers.

Figure 3:
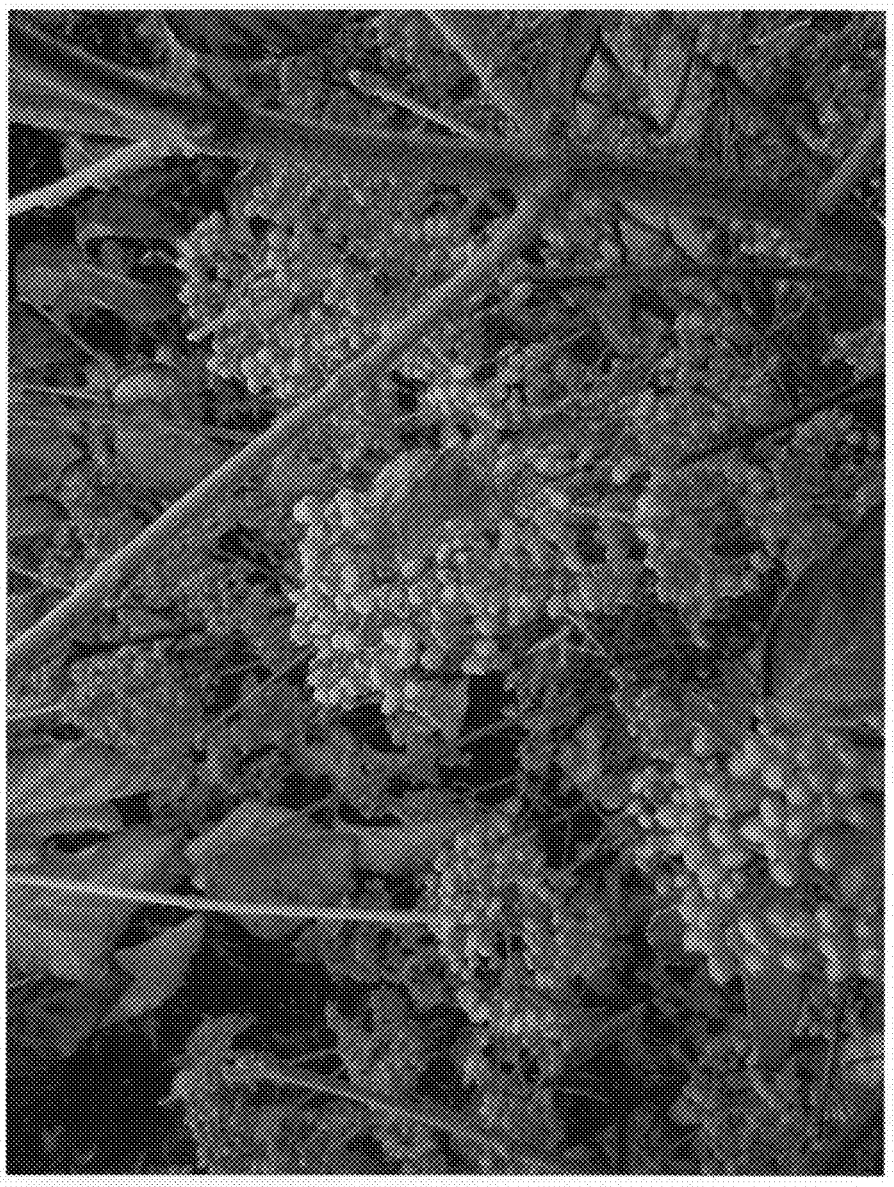

FIG. 3. Shows a close-up view of fruits and Fall foliage.

DESCRIPTION OF THE NEW CULTIVAR

In the following description, color references are made to The Royal Horticultural Society Colour Chart 2015 except where general terms of ordinary dictionary significance are used. The following observations and measurements describe 'SMNBDO' plants grown in a poly greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

DETAILED BOTANICAL DESCRIPTION

Botanical classification: *Viburnum dilatatum* 'SMNVD-MDO'.

Propagation:

Typical method: Softwood cuttings.

Time to initiate rooting: About 60 days at approximately 20° C.

Time to produce a rooted young plant: About 3 months at approximately 20° C.

Root description: Dense, somewhat free branching, fleshy roots of moderate thickness. Colored white, not accurately measured with an R.H.S. Chart.

Plant description:

*Age of plant described.*—About 2 years in a 3 gallon container.

*Growth habit.*—Perennial shrub. Upright and mounded.

*Height.*—40 cm in a 3 gallon container.

*Width.*—36 cm in a 3 gallon container.

*Growth rate.*—Moderate.

*Typical commercial container sizes.*—1, 2, and 3 gallon.

Branches:

*Branching habit.*—Basal branching freely.

*Lateral branch quantity.*—Average 32.

*Lateral branch length.*—Average 34 cm.

*Lateral branch diameter.*—Average 7.5 mm.

*Branch angle.*—Upright.

*Branch strength.*—Strong.

*Branch texture.*—Pubescent.

*Branch color.*—Mature Growth: Near Grey-Brown 199D. New Growth: Near Yellow-Green 146A.

*Internode length.*—7.0 cm on 1 year old stem, 4.0 cm on new growth, towards tips.

Foliage:

Leaves:

*Persistence.*—Semi-evergreen.

*Arrangement.*—Opposite.

*Length.*—Avg. range 8 to 12 cm.

*Width.*—Avg. range 7.5 to 11 cm.

*Shape.*—Broad ovate.

*Apex.*—Obtuse with a cuspidate tip on some leaves.

*Base.*—Cuneate.

*Margin.*—Dentate.

*Texture upper surface.*—Slightly fuzzy.

*Texture lower surface.*—Prominent reticulated veins.

*Color.*—Immature: Upper: Near Yellow-Green 144A. Lower: Near Green 143B. Mature: Upper: Near Green 139A. Lower: Near Green 137B. Fall foliage color: Upper: Near Greyed-Orange N167C, flushed 166A and 166B. Lower: Near Greyed-Orange N167D.

*Venation.*—Type: Pinnate. Color: Upper: Near Yellow-Green 153D. Lower: Near Yellow-Green 160C.

*Petiole.*—Length: Average range 1.0 to 1.5 cm. Width: Average 3.0 mm. Texture: Pubescent upper and lower surfaces. Color: New growth upper surface: Near Greyed-Yellow 160C. New growth lower surface: Near Greyed-Yellow 160C.

*Durability.*—Good durability to environmental stressors.

Inflorescence:

*Description.*—Single salverform flowers arranged in a terminal cyme.

*Flowering season.*—Early Spring beginning in early April.

*Flower longevity.*—2-3 weeks.

*Fragrance.*—Faint.

*Inflorescence per branch.*—Average range 1 to 5.

*Number of flowers per inflorescence.*—About 300 per cyme.

*Inflorescence height.*—Avg. 6.0 cm.

*Inflorescence diameter.*—Avg. 8.0 cm.

Flowers:

*Flower diameter.*—8 mm.

*Flower depth.*—5 mm.

*Flower angle.*—Upright facing.

*Persistent of self-cleaning.*—Self-Cleaning.

*Flower bud.*—Length: 1 cm. Diameter: 4 mm. Shape: Round. Color: Immature: Yellow 4C, mature Yellow-White 158B.

*Petals.*—Number: 5. Arrangement: Whorl. Length: Avg. 4 mm. Width: Avg. 3.5 mm. Shape: Obovate. Apex: Obtuse. Base: Fused. Margin: Entire. Texture: Glabrous, silky upper and lower surfaces. Color: Immature upper surface: White 155D. Immature lower surface: White 155D. Mature upper surface: White 155D. Mature lower surface: White 155D.

*Sepals.*—Number: 5. Arrangement: Whorl. Length: Less than 1 mm. Width: Less than 1 mm. Shape: Lanceolate. Apex: Acute. Base: Fused. Margin: Entire. Texture: Glabrous upper and lower surfaces. Color: Yellow-Green 145B, upper and lower surfaces.

*Peduncle.*—Length: Avg. 6.5 cm. Width: Avg. 1.5 mm. Color: Upper section Yellow-Green 152D, lower section 144A. Texture: Pubescent. Angle: Upright and outward. Strength: Moderate.

*Pedicels.*—Length: Avg. 1 mm. Diameter: Avg. 1 mm. Texture: Pubescent. Color: Yellow-Green 146C. Strength: Strong.

Reproductive organs:

*Gynoecium.*—Pistil number: 1. Pistil length: Less than 1 mm. Stigma shape: Three lobed. Stigma color: Grey, not accurately measured with R.H.S. Chart. Style length: Less than 1 mm. Style color: White, not accurately measured with R.H.S. Chart.

*Androecium.*—Stamen number: 5. Filament length: 1 mm. Filament color: Yellow-White 158A. Anther shape: Oblong. Anther length: 0.5 mm. Anther color: Yellow 6 B. Amount of pollen: Scant. Pollen color: Yellow 6B.

OTHER CHARACTERISTICS

Fruit: Approximately 60 to 300 per branch. Spherical drupe 5.5 mm long, 5.5 mm in diameter, colored Orange-Red N30B, smooth texture.

Seed: 1 seed per fruit. About 3.5 mm long, 1.75 mm wide. Ovate, colored grey/brown, not accurately measured with R.H.S. Chart.

Disease and insect resistance: No significant disease or pest resistance nor susceptibility have been observed.

Cold hardiness: Observed to tolerate temperatures between −31° C. and 38° C.

What is claimed is:

1. A new and distinct *Viburnum* plant named 'SMNVD-MDO' as illustrated and described herein.

* * * * *